United States Patent
Rajagopalan et al.

(10) Patent No.: US 11,650,192 B2
(45) Date of Patent: May 16, 2023

(54) DEVICE AND METHOD FOR MEASURING THE TOTAL ORGANIC CARBON CONTENT OF A SAMPLE FLUID

(71) Applicant: Merck Patent GmbH, Darmstadt (DE)

(72) Inventors: Pascal Rajagopalan, Palaiseau (FR); Julien Gross, Elancourt (FR); Pierre Caruso, Paris (FR)

(73) Assignee: Merck Patent GmbH

( * ) Notice: Subject to any disclaimer, the term of this patent is extended or adjusted under 35 U.S.C. 154(b) by 259 days.

(21) Appl. No.: 16/485,828

(22) PCT Filed: Feb. 20, 2018

(86) PCT No.: PCT/EP2018/054060
§ 371 (c)(1),
(2) Date: Aug. 14, 2019

(87) PCT Pub. No.: WO2018/153822
PCT Pub. Date: Aug. 30, 2018

(65) Prior Publication Data
US 2020/0003747 A1   Jan. 2, 2020

(30) Foreign Application Priority Data

Feb. 23, 2017 (EP) ..................... 17290024

(51) Int. Cl.
*G01N 33/18* (2006.01)
*B01L 3/00* (2006.01)
(Continued)

(52) U.S. Cl.
CPC .......... *G01N 33/1846* (2013.01); *B01L 3/508* (2013.01); *G01N 25/00* (2013.01);
(Continued)

(58) Field of Classification Search
CPC .. G01N 33/1846; G01N 25/00; G01N 27/045; G01N 27/06; B01L 3/508;
(Continued)

(56) References Cited

U.S. PATENT DOCUMENTS

| | | |
|---|---|---|
| 5,132,094 A | 7/1992 | Godec et al. |
| 5,275,957 A | 1/1994 | Blades et al. |

(Continued)

FOREIGN PATENT DOCUMENTS

| | | |
|---|---|---|
| CN | 2570774 Y | 9/2003 |
| CN | 1224840 C | 10/2005 |

(Continued)

OTHER PUBLICATIONS

Sievers 800 Series Total Organic Carbon Analyzer Operation and Maintenance Manual, DLM 30007-08 Rev. A, 2004, http://www.ecs.umass.edu/eve/facilities/equipment/OCD/DLM30007-08.pdf (Year: 2004).*

(Continued)

*Primary Examiner* — Robert J Eom
(74) *Attorney, Agent, or Firm* — Nields, Lemack & Frame, LLC (57) ABSTRACT

A device for measuring the total organic carbon content (TOC) of a sample fluid comprises a measuring cell (2) defining a volume (3) for containing a sample fluid and an excimer lamp (20) arranged to cause an oxidation reaction of the sample fluid by emitting radiation onto the sample fluid in the volume (3). A pair of electrodes is arranged to measure the conductivity of the sample fluid during the oxidation reaction and at least one temperature senor (31) is arranged on the measuring cell (2) to measure a temperature that is related to the sample fluid. The total organic carbon content (Continued)

(TOC) of the sample fluid is determined on the basis of the measured conductivity compensated by the temperature related to the sample fluid.

18 Claims, 6 Drawing Sheets

(51) Int. Cl.
  *G01N 25/00* (2006.01)
  *G01N 27/04* (2006.01)
  *G01N 27/06* (2006.01)
(52) U.S. Cl.
  CPC .......... *G01N 27/045* (2013.01); *G01N 27/06* (2013.01); *B01L 2300/06* (2013.01); *B01L 2300/0627* (2013.01); *B01L 2300/0645* (2013.01); *B01L 2300/0809* (2013.01); *B01L 2300/12* (2013.01); *B01L 2400/06* (2013.01)
(58) Field of Classification Search
  CPC ......... B01L 2300/06; B01L 2300/0627; B01L 2300/0645; B01L 2300/0809; B01L 2300/12; B01L 2400/16
  See application file for complete search history.

(56) References Cited

U.S. PATENT DOCUMENTS

| | | | | |
|---|---|---|---|---|
| 5,750,073 | A | 5/1998 | Godec et al. | |
| 6,183,695 | B1* | 2/2001 | Godec | G01N 27/4166 422/79 |
| 6,228,325 | B1* | 5/2001 | Godec | G01N 27/06 422/80 |
| 2003/0040122 | A1 | 2/2003 | Blades | |
| 2003/0211626 | A1 | 11/2003 | Davenport et al. | |
| 2008/0258742 | A1 | 10/2008 | Dimitrakopoulos et al. | |
| 2012/0180554 | A1 | 7/2012 | Leggett et al. | |
| 2014/0051156 | A1 | 2/2014 | Miyake et al. | |

FOREIGN PATENT DOCUMENTS

| | | |
|---|---|---|
| CN | 205844294 U | 12/2016 |
| CN | 106290722 A | 1/2017 |
| EP | 0153224 A1 | 8/1985 |
| JP | 2001-183357 A | 7/2001 |
| JP | 2003-53178 A | 2/2003 |
| JP | 2004-508551 A | 3/2004 |
| JP | 2004-521318 A | 7/2004 |
| JP | 2008-139312 A | 6/2008 |
| JP | 2012-63302 A | 3/2012 |
| JP | 2013-160611 A | 8/2013 |
| JP | 2014-59288 A | 4/2014 |
| WO | 97/21096 A1 | 6/1997 |
| WO | 03/038428 A1 | 5/2003 |

OTHER PUBLICATIONS

Japanese communication, with English translation, dated Aug. 30, 2021 in corresponding Japanese patent application No. 2019-545968.

Chinese communication, with English translation, dated Aug. 30, 2021 in corresponding Chinese patent application No. 201880013724.6.

International Search Report and Written Opinion dated May 8, 2018 in corresponding PCT application No. PCT/EP2018/054060.

Luan et al., "Structural, Photophysical and Photocatalytic Properties of Bi2MTaO7 (M = La and Y)", Journal of Materials Science, vol. 41, No. 23, pp. 8001-8012, Sep. 2006.

* cited by examiner

DEVICE AND METHOD FOR MEASURING THE TOTAL ORGANIC CARBON CONTENT OF A SAMPLE FLUID

The invention relates to a device and to a method for measuring the total organic carbon (TOC) content of a sample fluid, preferably of pure or ultra-pure water.

The monitoring of total organic carbon (TOC) in pure or ultrapure water having a conductivity of less than 1 µS/cm is a good indicator of the water quality and the correct operation of a purification process. Ultrapure water can be defined as the highest quality reagent grade water that exceeds ASTM D5127 standards and that has a total organic carbon (TOC) of less than five parts per billion (ppb).

The method is generally based on an oxidation of the organic carbon contained in a sample fluid and a subsequent detection of the resulting $CO_2$ (carbon dioxide) in the sample fluid. The oxidation of the sample fluid can be effected by UV-radiation. The amount of $CO_2$ is determined by measuring the conductivity of the sample fluid.

TOC measurements have been performed in the laboratory for more than 30 years. Over time the market demanded greater levels of sensitivity to determine significantly lower TOC concentrations.

Almost all common TOC monitors which are based on UV-oxidation are using a mercury gas lamp as radiation source. The lamp is arranged to irradiate an oxidation chamber where the sample fluid (e.g. a water sample) is trapped. During an oxidation reaction induced by the UV-irradiation the organics contained in the sample fluid are oxidized into carbonates. The conductivity or resistivity of the sample fluid is monitored and converted into an organic equivalent concentration of the TOC (in ppb) based on the known relationship between the two. Inside the oxidation chamber the water conductivity is monitored and must be compensated with the temperature. During the oxidation reaction, the static sample fluid is generally heated by the heat transmitted from the lamp but could be also cooled by the influence of static air surrounding the oxidation chamber. The influence of the temperature on the TOC computation is especially high at a conductivity between 0.1 and 1 µS/cm.

U.S. Pat. No. 5,275,957B discloses a sample cell for measuring the carbon content of water. The sample cell has a casing formed from Teflon with a fluid tight chamber, a first port connectable to a source of influent water into the fluid tight chamber, a second port through which the water can exit from the fluid tight chamber, and a quartz window closing off the fluid tight chamber from a mercury vapor lamp with a radiation at a primary wavelength of 253.7 nm and located in an adjacent chamber filled with dry nitrogen or another UV-non-absorbing gas. Two concentric circular electrodes made of titanium, palladium, iridium, rhodium or platinum are disposed within the chamber. A temperature sensor is attached to the rear of the central electrode and it is used to compensate for variation in the water conductance with temperature. The conductivity signal is monitored as a function of time while the sample fluid is static in the fluid tight chamber to indicate when the oxidation reaction has been completed. The document also discloses another sample cell that is constructed entirely of titanium and high-purity synthetic fused silica. The completion of the oxidation reaction is determined when either the first or second time derivative of the conductivity signal monitored as a function of time approaches zero.

WO 03/038428A1 discloses another example of a device for measuring the oxidizable carbon of a liquid. This device has a cell, two elongated probes penetrating a rigid outer wall of the cell extending into the cell's internal volume, and a temperature sensitive element positioned within a bore of one of the elongated electrodes. The outer wall is light-transmissive, for example synthetic fused silica or fused quartz material transmissive of 185 and 254 nm ultraviolet wavelengths which is the radiation range of the low pressure mercury vapor lamp proposed as the photo-radiation source.

Mercury lamps generally degrade quickly if switched ON and OFF frequently. Further, the mercury lamps require a typical pre-heating time of 30 s which delays work progress and limits efficiency. Finally, the operation and disposal of mercury lamps requires extreme care and high safety standards due to the hazardous toxic nature of the mercury.

JP 2001-183357A discloses an oxidizer assembly for a TOC measuring system. The oxidizer assembly includes one or two UV Excimer lamps which emit light at a wavelength of 184.9 nm and are respectively accommodated within a closed casing purged with inert N2 gas. The casing holding the excimer lamp is separated from an oxidation chamber by means of an optical window made of Magnesium fluoride (MgF). The oxidation chamber has a sample water inlet and a sample water exit to allow the sample water to flow through the chamber while the light of the excimer lamp(s) is transmitted through the optical window into the chamber to oxidize the sample water. This document does not describe details of a monitoring of conductivity or temperature.

An object to be solved is to provide a device and a method for measuring the total organic carbon content of a sample fluid, preferably of pure or ultra-pure water, which is improved with respect to sensitivity, accuracy, useful lifetime and/or measuring speed.

Another aspect is to avoid negative influences on the environment, i.e. persons in a laboratory, where the device and method are used.

In order to solve the problem described above the present invention provides a device for measuring the total organic carbon content of a sample fluid with the features of claim 1 and a method of measuring the total organic carbon content of a sample fluid with the features of claim 16. Preferred embodiments of the device and the method are defined in the respective dependent claims.

The device of the present invention for measuring the total organic carbon content of a sample fluid comprises: a casing that accommodates a measuring cell defining a volume for receiving the sample fluid, an excimer lamp arranged to emit radiation having a main wavelength that is suitable to cause an oxidation reaction of organic carbon compounds of the sample fluid contained within the volume of the measuring cell, a pair of electrodes arranged to measure the conductivity of the sample fluid in the volume of the measuring cell, and a first temperature sensor located on the measuring cell.

The excimer lamp that is provided as the radiation source provides the advantage that the main wavelength of the radiation available for the photo-irradiation and oxidation of the organics contained in the sample fluid is nearly instantly emitted after switching ON the excimer lamp, typically in less than 10 ms, because it does not require a preheating time. Since switching ON and OFF of the excimer lamp, e.g. during intermittent or repeated measurements, has no ageing effect and no negative influence on its operational lifetime, a degradation of the radiation source is not likely even if used in laboratory applications involving a high volume or throughput. In addition, the excimer lamp can be disposed as general electrical waste so that safety standards for operation and disposal of the device are low.

Due to the short wavelength of the radiation emitted by an excimer lamp, for example and especially preferred an excimer lamp emitting radiation having a main wavelength of between 150 nm and 200 nm, preferably a Xenon filled excimer gas lamp providing a mono main-wavelength of 172 nm, preferably with a half bandwidth of +/−8 nm, the organics contained in the sample fluid can be quickly and substantially completely oxidized, therefore, a detection level of TOC of below 1 ppb can be achieved.

According to a preferred embodiment of the present invention the device may further comprises at least one second temperature sensor which can be arranged to measure the temperature of the sample fluid at a location other than at the measuring cell, wherein the at least one second temperature sensor is preferably arranged to measure a temperature related to the sample fluid, preferably before the radiation induced oxidation reaction is started and/or at a location upstream of the volume of the measuring cell.

The possibility to measure the temperature during the oxidation reaction at different locations allows a more accurate determination of the temperature of the sample fluid based on a model of the device reflecting influence parameters that are predetermined by experiment. The temperature that is measured at the inlet of the sample fluid into the measuring cell and before the radiation induced oxidation reaction is started may be used as an initial temperature of the sample fluid. According to a still further preferred embodiment of the present invention the device may further comprise a control device configured to determine based on the conductivity and a temperature related to the sample fluid, that the oxidation reaction of organic carbon compounds in the sample fluid has stabilized, and configured to switch off the excimer lamp (20) in accordance with the result of determination.

Therefore, the device can dynamically stop the oxidation reaction by switching OFF the excimer lamp on the basis of the determination of the organic carbon content (TOC). In particular, the control device can switch OFF the excimer lamp when an oxidation reaction stabilization is reached, i.e. when a change rate of the TOC amount determined during the oxidation reaction is below a predefined threshold value. The dynamic stop of the radiation source provides the advantage that no unnecessary UV-radiation is emitted by the excimer lamp and therefore organic leaching from the measuring cell or other components of the device exposed to the radiation as well as generation of heat is reduced.

According to a preferred embodiment of the present invention the control device is configured to estimate the temperature related to the sample fluid in the volume of the measuring cell using the measuring result of the first temperature sensor and, if provided, of the second temperature sensor.

By using the temperature measurements from various locations on the device the temperature related to the sample fluid contained in the volume of the measuring cell may be estimated with an accuracy that is close to that of an in situ probe placed inside the sample fluid within the measuring cell. The more precise determination of the temperature related to the sample fluid can be used to more accurately calculate the TOC of the sample fluid in that the temperature compensation of the conductivity measured by the two electrodes in the sample fluid is improved. As a result, it becomes possible to precisely detect very small TOC contents of down to about 1 ppb as is required in case the TOC of ultrapure water is to be measured.

According to a preferred embodiment of the present invention the device may be provided with at least one valve arranged to block a flow into or a flow out from the measuring cell. With the valve the flow into and out from the volume of the measuring cell can be controlled (e.g. completely stopped). Therefore, an intermittent measuring process can be executed.

According to a still further embodiment of the present invention at least a part of an internal surface of the device exposed to the radiation from the excimer lamp may comprise a compound that can transform the radiation from the excimer lamp into a radiation having at least one wavelength that is different from the main wavelength, preferably longer and preferably in the range between 180 nm and 280 nm, preferably around 190 nm and around 250 nm.

The wavelength of around 250 nm is well known to destroy the ozone formed during operating of the excimer lamp in the chamber accommodating the measuring cell. Thus, the concentration of hazardous ozone within the device can be reduced.

According to a further preferred embodiment of the present invention the compound may include at least one element of the Lanthanides group, preferably Lanthanum, Praseodymium or Neodymium, in association with at least one of Yttrium, Phosphate or Aluminum Borate.

According to a still further preferred embodiment of the present invention the device may further comprise a catalyzing substance provided in the interior space of the casing of the device to accelerate the decomposition of ozone within the chamber. The catalyzing substance may be provided in the interior space of the upper casing part 13 or of the lower casing part 14 of the device. The ozone self-decomposition can be accelerated by a catalytic effect of the catalysing means. This effect may be combined with other decomposition effects of ozone such as a thermal decomposition effect and the like.

According to a further preferred embodiment of the present invention the catalyzing substance may comprise Platinum, Palladium, Copper (II) oxide, activated Carbon, Manganese dioxide or a combination thereof.

According to a preferred embodiment of the device of the present invention the catalyzing substance may be provided in the form of a paint, a coating, pellets, beads, powder, a 2D or 3D mesh, a plate, a sheet, a foam, a porous structure or as a combination thereof.

The catalyzing substance may for example be a coating (for example manganese dioxide) on a substrate (for example a foam).

According to a still further embodiment of the present invention the measuring cell is made from or includes quartz permeable for the radiation in the range of at least between 150 nm and 280 nm. That is, the measuring cell is transparent within the UV spectrum of interest of the radiation of the excimer lamp.

According to a further preferred embodiment of the present invention the volume of the measuring cell is less than 1.0 ml, preferably less than 0.5 ml. Therefore, the radiation emitted by the excimer lamp can cause the oxidation reaction throughout the sample fluid stored within the measurement cell.

The method of measuring the total organic carbon content of a sample fluid using the device according to the present invention comprises the steps of: supplying the sample fluid into the volume of the measuring cell, stopping the inflow into the volume, operating the excimer lamp, maintaining the sample fluid in the volume of the measuring cell while the excimer lamp is in operation, determining the total organic carbon content of the sample fluid on the basis of the conductivity and the temperature related to the sample fluid, switching off the excimer lamp in accordance with the result of determination, preferably when it is determined that the oxidation reaction of organic carbon compounds in the sample fluid has stabilized, and discharging the sample fluid from the volume of the measuring cell.

According to the method of the present invention it is possible to detect even low concentrations of about 1 ppb of TOC in the sample fluid, i.e. is suitable for measuring the TOC of ultrapure water.

According to a preferred embodiment the method may further comprise the step of estimating the temperature of the sample fluid using the measuring result of the first temperature sensor and, if provided, of the second temperature sensor, and using this estimated temperature as the temperature related to the sample fluid.

First, the general background of the oxidization reaction used to determine the total organic carbon content (TOC) of a sample fluid, on which the device and method of the invention are based, is briefly summarized. The device and method are specifically suitable for use in the TOC determination of pure or ultrapure water but the invention is not limited in this respect.

Determination of TOC by Oxidization Reaction

An oxidization reaction induced by radiation which is also known as a photo-oxidation reaction will take place in a fluid containing organic carbon when it is exposed to radiation with a wavelength below 200 nm. Therefore, the invention employs a radiation source suitable to emit wavelengths lower than 200 nm. Upon irradiation the organic carbon compounds contained within the sample fluid oxidize and carbon dioxide ($CO_2$) is formed. While the oxidation reaction takes place, the conductivity and the temperature of the fluid is continuously or intermittently measured and monitored. Since the temperature of the sample fluid has an influence on the conductivity, both measurements (conductivity and temperature) are considered in order to determine the temperature compensated conductivity based on which the total organic carbon (TOC) content of the sample fluid can be determined from a known relationship. The basic principle of the TOC determination process based on conductivity and temperature is known and is, for example, described in U.S. Pat. No. 5,275,957B.

Hereinafter, embodiments of the present invention will be described with reference to the accompanying drawings.

As shown in FIGS. 1 to 5 a device 1 for measuring the total organic carbon content of a sample fluid comprises a casing 10 formed by an upper casing part 13 and a lower casing part 14. The upper casing part 13 and the lower casing part 14 can be made as separate parts and coupled to each other by fastening means like bolts or a clamp or the like. Between the upper casing part 13 and the lower casing part 14 a gasket 15 is provided to seal an interior space 9 of the casing 10 in an assembled state from the environment (see FIG. 5). This means that the interior space 9 is composed of the air within part 13 and part 14. In an alternative embodiment the casing 10 may be also formed from more than two parts and assembled together and the interface(s) where the various parts are connected to form the casing may be located as desired and sealed by gaskets as necessary. The gasket is formed from PTFE for example and is in this embodiment a flat sheet sealing the entire periphery of the interface between the upper and lower casing parts and including a window aperture 17 (see FIG. 5) for passing radiation from one casing part to the other as described later.

Figure 1:
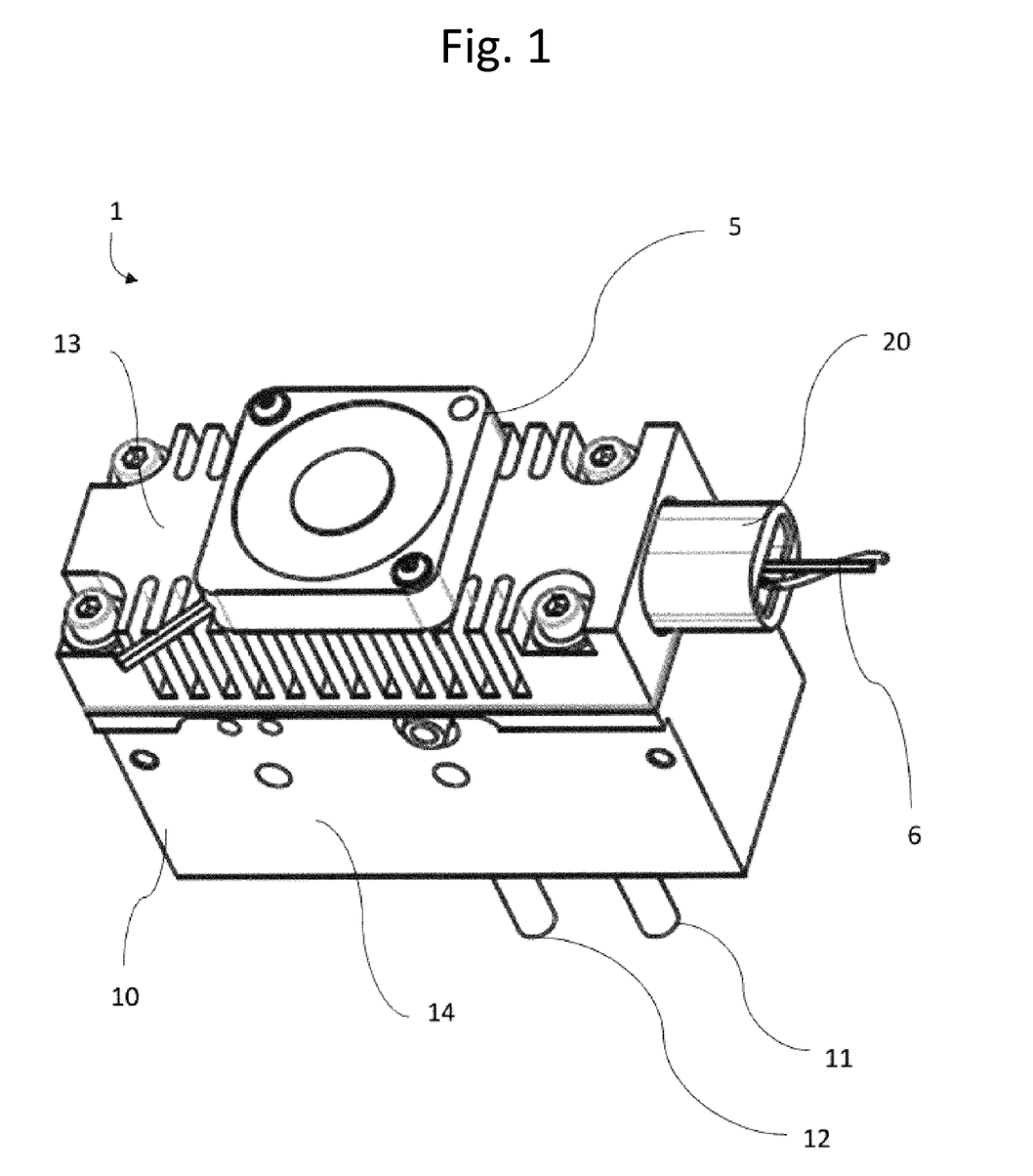
FIG. 1 is a perspective view of a device for measuring the total organic carbon content of a sample fluid according to an embodiment of the present invention.
Figure 2:
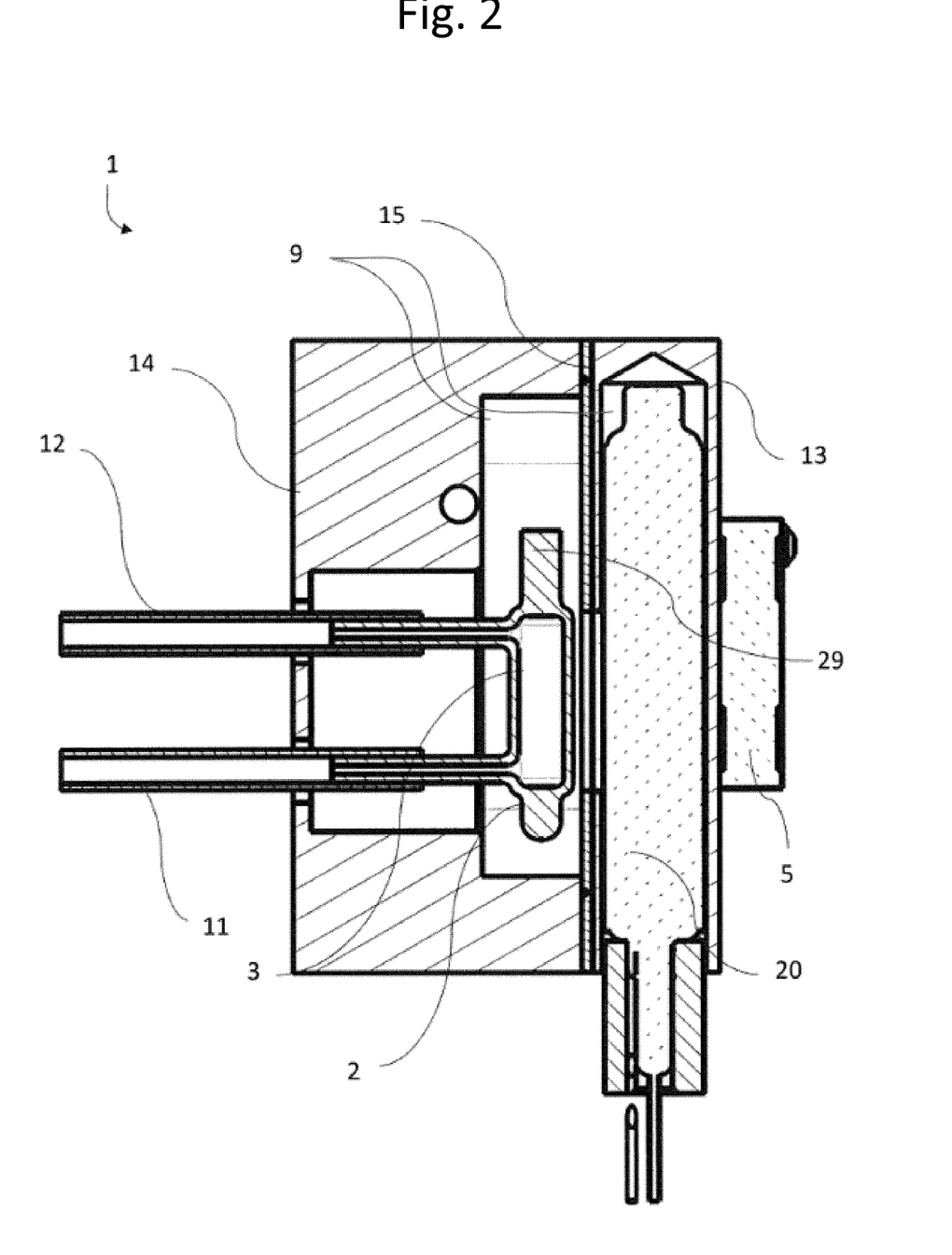
FIG. 2 is a sectional view of the device according to the embodiment of the present invention.
Figure 3:
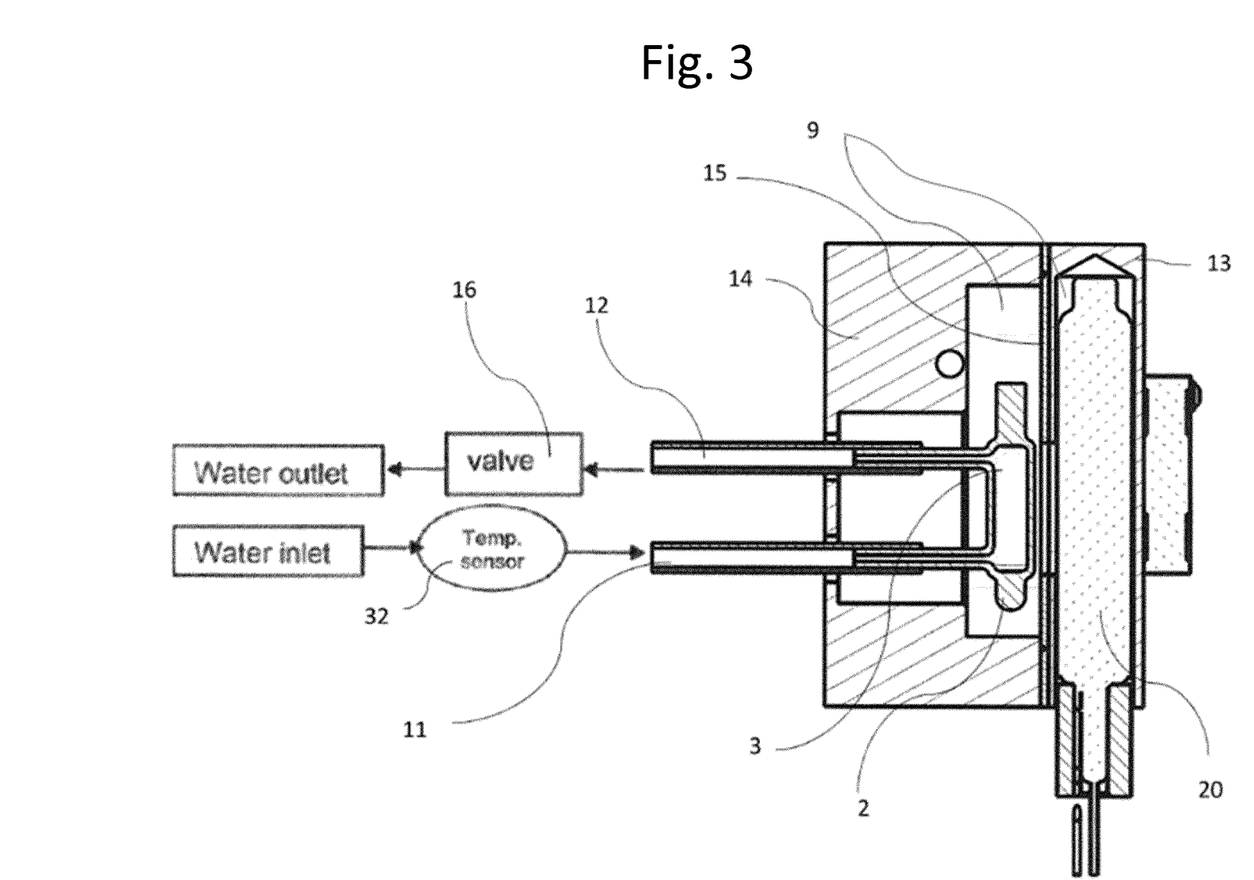
FIG. 3 is a sectional view of the device for measuring the total organic carbon content of a sample fluid according to an embodiment of the present invention with peripheral components.
Figure 5:
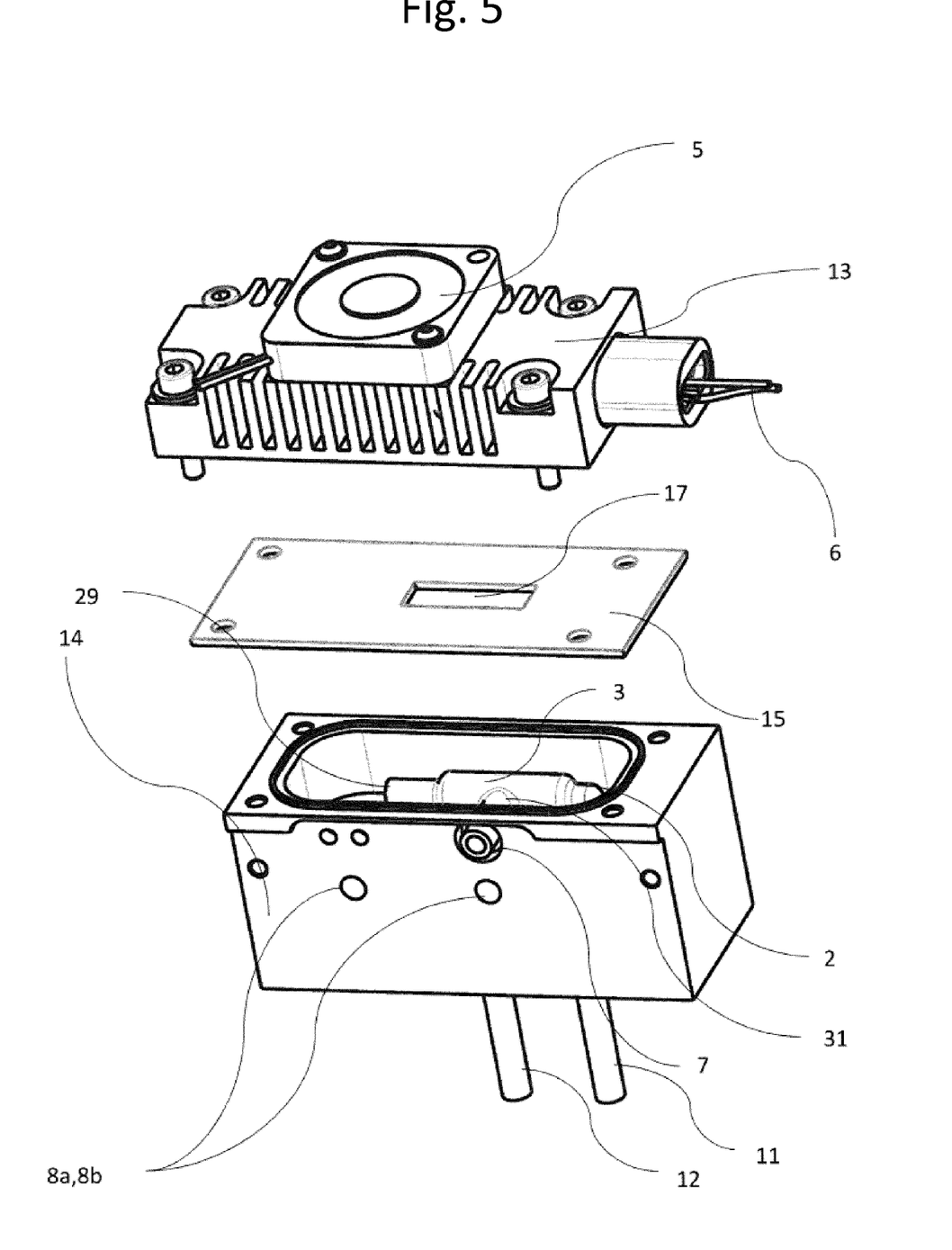
FIG. 5 is a perspective exploded view of the device according to the embodiment of the present invention.

As shown in FIGS. 2, 3 and 5 the casing 10 accommodates in its interior space or chamber 9 a measuring cell 2 defining a volume 3 for receiving the sample fluid for the measuring process. The measuring cell 2 is provided with a fluid inlet 11 for introducing the sample fluid into the volume 3 of the measuring cell 2 and with a fluid outlet 12 for discharging the sample fluid from the volume 3 of the measuring cell 2. In the particular embodiment shown in the drawing a two-part design of the casing 10 is chosen and the measuring cell 2 is located in the lower casing part 14 to form a cell-sub assembly and a radiation source to be described later is located in the upper casing part 13 to form a lamp-sub assembly. The casing parts 13, 14 can be made of aluminum, steel, resin or the like. The casing parts, if made from aluminum, can be black anodized.

Figure 4:
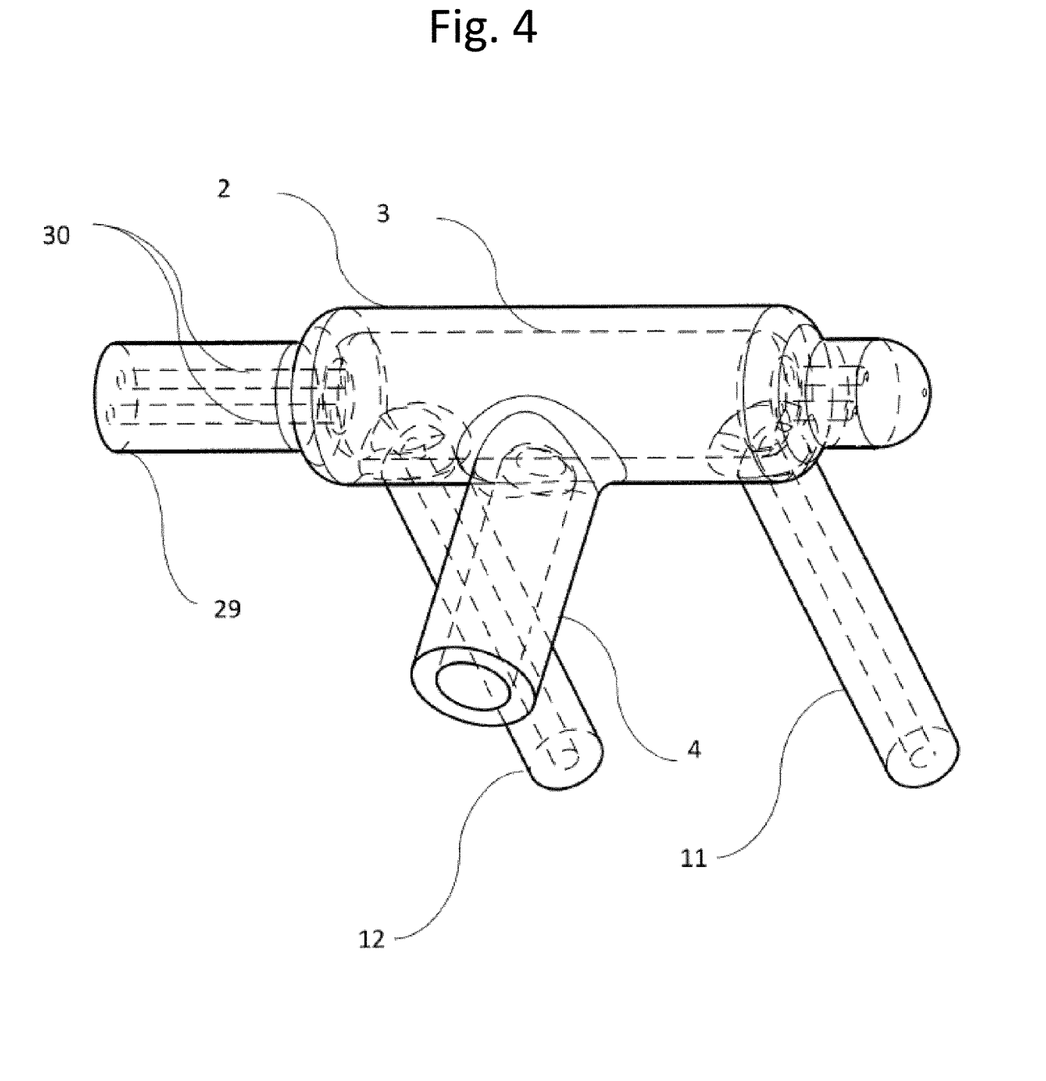
FIG. 4 is a perspective view showing schematically a measuring cell according to an embodiment of the present invention.

As shown in FIG. 4 the measuring cell 2 is in the form of an elongated receptacle with a small diameter in which the volume 3 for receiving the sample fluid extends in the longitudinal direction from the inlet 11 to the outlet 12. At one side of the measuring cell 2 a chamber 4 for receiving a temperature sensor to be described later is disposed. The chamber 4 is separated and isolated from the volume 3. The chamber 4 may be glued onto the measuring cell 2. Alternatively, the chamber 4 may be integrally formed with the measuring cell 2. In addition, at one end of the measuring cell 2 a housing 29 for accommodating a pair of electrodes (to be described later—not shown in the drawing) to be inserted into holes 30 is disposed, preferably integrally formed with the measuring cell 2. More precisely, the housing 29 accommodates the pair of electrodes in the holes 30 such that they are able to measure a conductivity of the sample fluid contained inside the volume 3.

The opposite side of the measuring cell 2 in its longitudinal direction with respect to the housing 29 may have a hemispherical end cap. Specifically, the pair of electrodes may extend from the housing 29 into the hemispherical end cap to be supported therein. The functional part including the volume 3 and the chamber 4 for the sensor of the measuring cell 2 at least but preferably the entire measuring cell 2 with the inlet, outlet, the hemispherical end cap and the housing 29 is preferably made from a quartz material. The quartz material is arranged such that it is permeable for radiation, preferably for radiation in the ultraviolet and infrared spectral ranges, preferably in the range of at least between 150 nm and 280 nm. Nevertheless, the housing 29, the chamber 4, the hemispherical end cap, the inlet 11 and the outlet 12 may include an ingredient that is configured to block UV-radiation. For example, this ingredient may be an element of the lanthanide group, preferably cerium. That is, the quartz material may be doped with cerium.

Quartz glass is formed from silica in amorphous (non-crystalline) form and differs from traditional glasses in that it does not contain other ingredients which are typically added to glass to lower the melt temperature. Quartz glass also has a high melting point (compared to ordinary glass), a high chemical purity and resistance, a high thermal resistance, a low thermal expansion with high resistance to thermal shocks, and a high radiation resistance.

In an alternative structure the measuring cell 2 may also have the quartz glass only in the form of a window to let radiation pass into the interior of the volume 3 where the sample fluid is received.

The volume 3 of the measuring cell 2 is less than 1.0 ml, preferably less than 0.5 ml and it is located such that the radiation from the radiation source located in the interior space 9 of the casing 10, here in the lower casing part 14, can effectively enter the volume 3. Where the gasket 15 is placed between the casing parts, the volume 3 of the measuring cell 2 is located immediately below the window 17 so that other parts of the measuring cell are substantially shielded from the radiation while the volume extends substantially parallel to the excimer lamp described below. The relative small size of the volume 3 helps shortening the oxidation phase and enables a fast and highly sensitive response and sub-ppb TOC detection in a short time.

The upper casing part 13 accommodates the radiation source in the form of an excimer lamp 20 arranged to emit radiation having a main wavelength that is suitable to cause the oxidation reaction of organic carbon compounds in the sample fluid contained within the volume of the measuring cell 15. The excimer lamp 20 (or "excilamp") is a source of ultraviolet light produced by spontaneous emission of excimer (exciplex) molecules. The main wavelength that is emitted by the excimer lamp 20 depends on the working gas of the excimer lamp. Lamp wires 6 for supplying the lamp with the necessary operating voltage are guided through a sealed port in the upper casing part 13 (see FIGS. 1 and 2).

Excimer lamps are quasi-monochromatic light sources that can operate over a wide range of wavelengths in the ultraviolet (UV) and vacuum ultraviolet (VUV) spectral regions with high power spectral density. The operation of excimer lamps is based on the formation of excited dimers (excimers) and the following transition from the bound excited excimer state to a weakly bound ground state resulting to an UV-photon radiation. An excimer lamp radiation wavelength is specified by the working gas also known as an excimer molecule such as Xenon gas ($Xe_2$).

Further, the excimer lamp is electrodeless and the discharge is based on radiofrequency energy. Thus, this lamp has no ageing effect linked to its being switched ON and OFF. Compared to a mercury lamp which requires a pre-heating time of approximately 30 s, the excimer lamp is essentially instantaneously operational, i.e. in less than 10 ms. For example, if the Xenon gas ($Xe_2$) is provided as working gas, the emitted radiation has a main wavelength of 172 nm. On the other hand, if Krypton is used as the working gas, the main wavelength would be 146 nm. Moreover, the excimer lamp can be disposed as general electrical waste and does not require a special treatment or disposal procedures.

The casing 10, preferably the upper casing part 13 may be provided with a heat sink for efficiently dissipating the heat of the excimer lamp 20 generated during operation away from the device 1. The heat sink may be an active and/or passive cooling system like an electrical fan 5 attached to the top surface of the upper casing part (see FIG. 1), cooling ribs, a radiator, a heat-pipe or the like.

The excimer lamp 20 is located inside the casing 10 such that the radiation is emitted into the space 9 holding the measuring cell 2. Since the main wavelength of the radiation is short (e.g. 172 nm), there is a strong absorbance of UV-radiation in the air. Therefore, a distance between the excimer lamp 20 and the measuring cell 2 in the space 9 inside the casing 10 is set as small as possible, preferably to less than 1 mm, to reduce any obstacles or absorbing influences on the radiation between the excimer lamp 20 and the volume 3 of the measuring cell 2.

The main wavelength of the radiation of the excimer lamp 20 is preferably below 200 nm, preferably between 150 nm and 200 nm, most preferably 172 nm in case pure Xenon gas is used, preferably with a half bandwidth of +/−8 nm relative to the peak intensity, wherein there is still more than 50% of the peak intensity in the range of 164 nm to 180 nm. As mentioned before the wavelength is depending from the working gas in the excimer lamp. Other eligible working gases producing radiation in the desired range are Ar, Kr, $I_2$, $F_2$.

The measuring cell 2 accommodates the pair of electrodes embedded into holes 30 in the quartz material and arranged to measure the conductivity of the sample fluid in the volume 3 of the measuring cell 2.

As described above the first temperature sensor 31 is located on the measuring cell 2, for example in that it is inserted into the chamber 4 in the measuring cell 2 that is separated and isolated from the volume 3. The sensor 31 may be inserted into chamber 4 from the outside of the casing 10 through an opening 7 as indicated in FIG. 5. The first temperature sensor 31 is used to measure the temperature of the measuring cell 2 and it may be a thermistor or the like. The first temperature sensor 31 may be fixed on the measuring cell 2, for example, by glue such as a thermally conductive epoxy. The temperature measurement of the first sensor 31 is considered as a temperature related to the temperature of the sample fluid and it can be used to determine the temperature compensated conductivity of the sample fluid in the process of calculating the TOC thereof.

According to a preferred embodiment of the invention, as shown in FIGS. 3 and 5, the device 1 may comprise at least one second temperature sensor 32, again in the form of a thermistor or the like. The at least one second temperature sensor 32 can be arranged to measure a temperature related to the sample fluid at another location, preferably before the radiation induced oxidation reaction is started and/or at a location at or upstream of the inlet into the volume 3 of the measuring cell 2 (as shown in FIG. 3) e.g. in the water flow and/or at one or more other locations at the casing or the measuring cell 2 of the device 1 as indicated by the reference numerals 8a, 8b in FIG. 5. The measuring result of the one or more further temperature sensors 32 will be used in a control device described below to deduct the temperature of the sample fluid more accurately and approximate the accuracy of the temperature determination to that of an in situ thermal probe measurement, thereby improving the accuracy of the temperature compensation of the conductivity measurement especially for sub ppb TOC detection as in case of ultrapure water. For example, in a water sample with a resistivity of 1 MOhm*cm an error of 100 can bring 11 ppb difference in TOC.

Control Device

The control device is configured to control a measuring process of TOC determination in that it is configured to determine, based on the conductivity measurement of the sample fluid in the volume 3 by means of the electrodes and the measurement of the temperature related to the sample fluid (to compensate the temperature influence on the conductivity), that the oxidation reaction of organic carbon compounds in the sample fluid has stabilized and it is configured to end the measuring process when the stabilized state is detected.

In addition, the control device is configured to execute the measuring process in which prior to each measurement of conductivity and temperature the excimer lamp 20 is switched off for a predetermined first period of time e.g. for 25 ms. After the measurement of conductivity and temperature is done the excimer lamp 20 is switched ON again. This cycle may be repeated, for example, every ten seconds until the control device determines that the stabilization of the oxidation reaction has been reached as described above. The switching OFF of the excimer lamp reduces the dose of UV radiation to the necessary duration and reduces heat input into the sample fluid and organic leaching from the cell as well as ozone production to the minimum necessary for an accurate determination of the TOC. In combination with the fast reaction of the excimer lamp this effect is even more remarkable. Moreover, the accuracy and precision of the measurement may be improved by measuring only during periods where the excimer lamp 20 is switched OFF.

Figure 6:
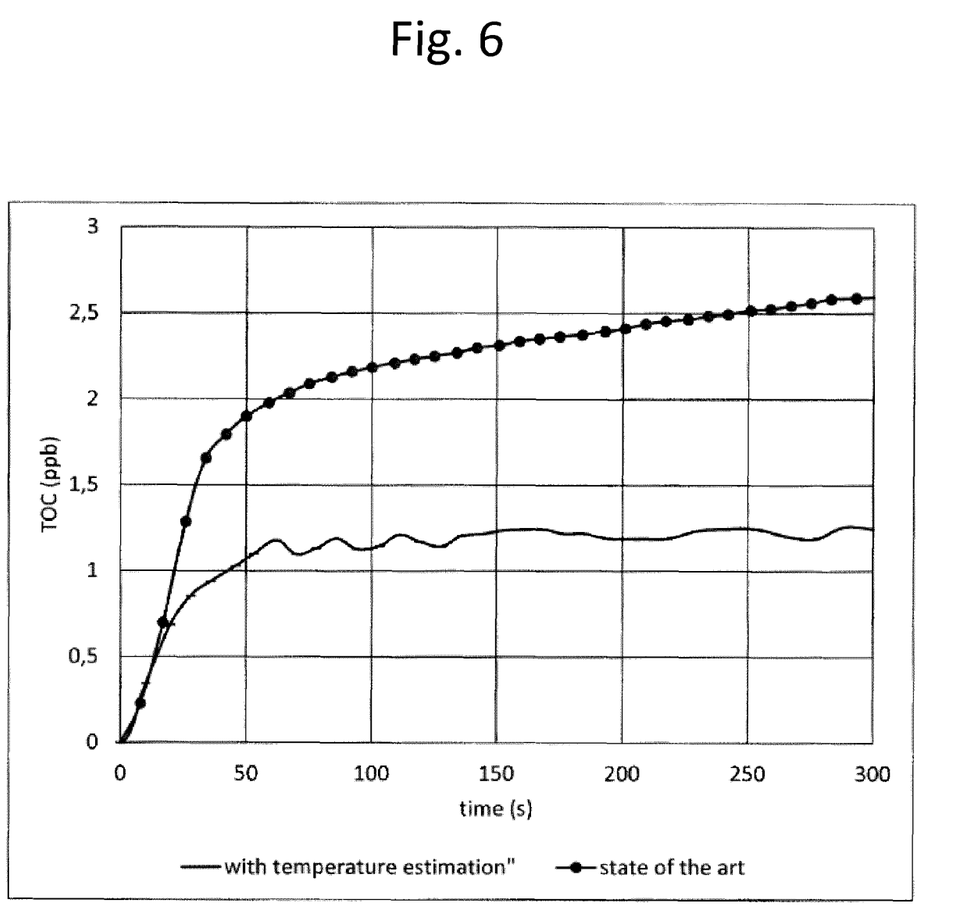
FIG. 6 is a diagram showing a first graph indicating an amount of TOC relative to the duration of a measurement according to an embodiment of the present invention and a second graph indicating the same measurement according to a technique of the state of the art.

FIG. 6 shows a diagram indicating the amount of TOC (on the abscissa) relative to the duration of measurement (on the ordinate) in a first graph showing the TOC calculated with a temperature compensation using the temperature determined by a temperature estimation of the invention based on plural temperature measurements (to be explained later) and in a second graph showing the TOC calculated with a method according to the state of the art.

In FIG. 6 on the left side of the diagram (at time 0) the oxidation reaction is started, i.e. the time at which the excimer lamp 20 is switched ON. After a certain duration (approximately after 70 s in the diagram) a stabilization of the TOC occurs. Stabilization in this connection describes a state where the changing of the TOC over time is relative low compared to the beginning of the oxidation reaction. As soon as the stabilization state is detected (i.e. by evaluating the first or second time derivatives reaching zero), the control device ends the measuring process. It is apparent that, due to the fact that the excimer lamp does not require a preheating time, the cycle time from switching ON of the lamp and starting of the oxidation reaction to the end of the reaction and the determination of the TOC value of the sample fluid can be shortened.

Depending on the TOC oxidation curve, i.e. the gradient, the oxidation device may optionally classify the type of sample fluid to be easy or difficult to oxidize.

Improved Temperature Estimation

Because no direct temperature measurement of the sample fluid in the volume 3 of the measuring cell 2 is possible the control device is configured to execute the temperature estimation using the measuring result of the first temperature sensor 31 located on the measuring cell 2 and of the second temperature sensor(s) 32, at least one arranged to measure the inlet temperature of the sample fluid as shown in FIG. 3, to more accurately estimate the temperature related to the sample fluid in the volume 3 of the measuring cell 2.

The temperature related to the sample fluid may be calculated according to the following equation:

$$T = \frac{1}{1 + \frac{MCp}{KS}s}\left(T_q + \frac{Phi}{KS}\right)$$

with $$Phi = \frac{1 + \tau_1 s}{(1 + \tau_2 s)(1 + \tau_3 s)} \alpha U$$

Wherein:
T=temperature related to the sample [K] (initial value measured by temperature sensor 32)
Phi=thermal power received by water from UV lamp [J/K]
$\tau_1$=first time constant [s]
$\tau_2$=second time constant [s]
$\tau_3$=third time constant [s]
$\alpha$=calibration factor [−]
U=voltage of the lamp 20 [V]
s=laplacian transform complex variable [−]
KS=thermal exchange coefficient between water and quartz [W/K] with
S=surface area of water in contact with the quartz [m$^2$] and
K=exchange coefficient by conduction of the water [W/(m$^2$*K)],
MCp=Thermal inertia (or capacity) of the water sample [J/K] with
M=mass representing cell geometry [kg] and
Cp=heat capacity (taken from the literature) [J/(kg*K)]
Tq=Temperature of the measuring cell 2 [K] (measured by temperature sensor 31)
$\alpha$=constant factor [−] (determined by experiment to allow a calibration if needed to take into account UV lamp dispersion)
Three time constants ($\tau_1$, $\tau_2$, $\tau_3$) have been introduced because the lamp power is not constant over time.

The equation is a reduced model representing a capacity consideration, wherein water (in this case the sample fluid) is exchanging heat with a heat source (in this case the location of the quartz measuring cell where the first temperature sensor 31 is located) and the heat transmitted by the excimer lamp 20. That is, the sample fluid is exchanging heat with the measuring cell 2 of which the temperature (Tq) is known from the measurement by the first temperature sensor 31, and with the excimer lamp 20 of which the operational state, i.e. the voltage input (U), the calibration factor ($\alpha$) and the time constants ($\tau_1$, $\tau_2$, $\tau_3$) are known. The further parameters of this model (MCp, KS,$) are determined by experiment or taken from the literature. Tq and U are known by measurement. The lamp ON command information is used to know if the oxidation reaction has commenced and start of the temperature estimation is desired.

The temperature estimation allows operation of the device 1 in warm environments (e.g. 65° C.) without performance and accuracy degradation as compared to conventional TOC measurement devices considering only a temperature input from a single temperature sensor. That is, by using two temperature sensors 31,32 (one in the water flow, e.g. upstream of the measuring cell 2) a rinsing time may be reduced as compared to conventional TOC measurement devices considering only a temperature input from a single temperature sensor because the influence of the measuring cell 2 temperature becomes negligible. In other words, the time reduction is attained because by using two temperature sensors 31,32 there is no need to cool the temperature of the measuring cell 2 down with fresh incoming water. The measuring process is controlled by the control device and executed as described above.

Alternative Embodiment

During the oxidation reaction the temperature of the excimer lamp 20 may reach more than 100° C. in the device including a heat sink or even 190° C. in a device without the heatsink described above. This heat dissipation may generate a significant error in the estimation of the temperature related to the sample fluid estimated only on the basis of the first temperature sensor 31.

The use of one or more second temperature sensor(s) 32 monitoring of temperature(s) at various positions on the device (i.e. at the casing parts 13, 14 or the interior space 9) and/or of the sample fluid upstream of the volume 3 of the measuring cell 2 (during filling of the volume or during initial rinsing of the volume in preparation of the TOC determination, i.e. prior to the oxidation reaction) and/or of the ambience allows the deduction of the temperature related to the sample fluid with an accuracy comparable to that of an in situ thermal probe.

The estimation of the temperature related to the sample fluid may be made based on a set of linear equations of the various measured temperatures considering mainly the localisation of the sensors, which set of linear equations can be experimentally determined in advance for the respective device configurations.

Experiments have shown that, using the temperature estimation described above, the error of the temperature related to the sample fluid during oxidation can be reduced below 0.8° C. after 100 s.

Reducing the environment exposure to ozone

Ozone is generated as a by-product in the surrounding air of the excimer lamp 20 due to its emission of radiation having the specific low wavelength. Ozone is particularly dangerous for human health when it leaks out of the casing 10 of the device. It could also cause premature ageing of the materials in contact. In order to reduce the ozone gas generated in the device 1 the invention provides various countermeasures.

According to one embodiment the present invention provides on at least a part, preferably substantially all of the internal surfaces of the interior space 9 of the device 1 that will be exposed to the radiation from the excimer lamp 20 in operation with a compound that can transform the radiation into a radiation having at least one wavelength that is different from the main wavelength thereof. The compound having this effect can be applied as a coating on the surfaces of the casing 10 surrounding the interior space 9 of the casing 10, preferably by vacuum sputtering. To be specific, the upper casing part 13 that surrounds the lamp 20 can also be coated as it can be in direct contact with the lamp. Thus, the 172 nm photons reaching the upper part 13 of the casing instead of being lost internally into heat can be transformed into the higher wavelength, The compound absorbs a fraction of the incident radiation which excites at least one electron of the compound and forces it to jump to a higher energy level. When the at least one excited electron falls back to its initial energy state, it emits the radiation with one or more wavelengths that is/are different from the exciting main wavelength.

In case of a main wavelength of radiation of 172 nm the wavelength of the radiation created by this process is in the range between 180 nm-200 nm or 240 nm-280 nm, preferably around 190 nm or around 250 nm and thus has a longer wavelength than the main wavelength. Since the decomposition of ozone by UV-radiation is maximized at a wavelength of 254 nm, the transformed radiation accelerates the self-decomposition of ozone and removes the ozone molecules that are generated in the chamber 9 of the casing 10 by the radiation from the excimer lamp 20.

The radiation having a higher wavelength is able to reach deeper into the sample fluid contained inside the volume 3. Thus, the hole sample fluid within the volume 3 will receive more radiation (UV energy). Therefore, an acceleration of the UV degradation is attained. Without these higher wavelengths there may be a limitation of the kinetics of the oxidation reaction because of radicals diffusion inside of the volume 3.

Suitable compounds include at least one element of the Lanthanides group, especially Lanthanum (La), Praseodymium (Pr) and Neodymium (Nd), in association with Yttrium, Phosphate or Aluminum Borate. An example of a compound which has the property to transform the 172 nm wavelength into the higher wavelength of 180 nm to 200 nm (~190 nm) or around 240 nm to 280 nm (~250 nm) with a coating thickness between 1 to 40 micrometer is the light emitting compound of formula: $(Ca_{1-x2y}Sr_x)Li_2Si_{1-z}Ge_zO_4$: $Ln_nM_y$ (where $L_n$=Ce3+, Pr3+, Sm3+, Eu3+, Gd3+, Tb3+, Dy3+, Er3+, Tm3+ or Yb3+; M=Na+, K+ or Rb+; x=0-0.1, y=0.001-0.2; and z=0-1) which is disclosed for example in EP 153224A1 for disinfection or sterilization application to be coated directly in the lamp, i.e. above or inside the quartz.

Other compounds which have the property to absorb radiation from the excimer lamp 20 and emit radiation with higher wavelengths of 180 nm to 200 nm (~190 nm) or around 240 nm to 280 nm (~250 nm) can be used as the coating on the inner surfaces of the chamber 9 that are exposed to the radiation of the excimer lamp 20 in order to destroy the ozone formation. The ozone molecules absorb UV light between 200 nm and 300 nm which results in splitting of the ozone into a molecule of $0_2$ and an oxygen atom. The oxygen atom then joins up with an oxygen molecule to regenerate ozone. This is a continuing process that terminates when an oxygen atom recombines with an ozone molecule to make two $0_2$ molecules: $20_3 \rightarrow 30_2$. Thus a low level of ozone in the air in the chamber 9 exposed to the radiation of the excimer lamp 20 is maintained, thus avoiding that ozone leaks out from the device during operation or maintenance.

Thus, the provision of the above compounds on some or all surfaces of the chamber 9 in which the measuring cell is located reduces the level of ozone produced in the device 1 and increases the lifetime of the materials in contact with the ozone. Moreover, the longer wavelengths emitted by the compounds can penetrate deeper into the sample fluid and thus increase the oxidation rate of the sample fluid. Further, the broader UV-C spectrum is provided in the chamber of the device that enlarges the scope of chemical bond energy dissociation.

Alternatively, or additionally, the device may further comprise a catalyzing substance provided in the chamber 9 of the casing 10 of the device 1 to accelerate the decomposition of ozone within the chamber 9.

It is known that a catalytic effect can accelerate ozone self-decomposition which can be combined with a thermal decomposition or other effects in order to accelerate the self-decomposition of ozone. The catalyzing substance is arranged in the chamber 9 of the device 1 such that the ozone generated in the chamber 9 by operating the excimer lamp 20 can come in contact therewith.

Suitable and effective catalyzing substances comprise Platinum, Palladium, Copper (II) oxide, activated Carbon, Manganese dioxide ($MnO_2$) or combinations thereof. A typical and effective catalyzer for ozone decomposition in air/gas is Manganese dioxide ($MnO_2$). Other metal oxides may also show the catalytic effect but are less efficient. CuO can be mixed with $MnO_2$ for efficiency and durability and such mixture is already known and commercialized as industrial catalyzer.

The catalyzing substance can be provided in the chamber 9 in the physical form of a paint or a coating of wall surfaces, pellets or beads, a powder or a foam received in the space surrounding the measuring cell, a 2D or 3D mesh, a plate, a sheet or a porous structure located in the chamber so as to not impede the radiation hitting the volume of the measuring cell or as combinations thereof.

In other variations the excimer lamp 20 may be impregnated with the substance or a ground mesh included in the excimer lamp 20 can be made of the substance or may include such a substance.

Method of measuring the total organic carbon content of a sample fluid

The method of measuring the total organic carbon content of the sample fluid using the device according to the present invention is an intermittent process similar to the one described in U.S. Pat. No. 5,275,957B. The process thus comprises an initial step of rinsing the volume of the measuring cell in order to prepare the measuring cell for the actual measuring cycle. Then, the sample fluid is supplied into the volume 3 of the measuring cell 2, the inflow is stopped (for example by closing a valve 16 located in the inlet or outlet pipe for the sample fluid) once the volume 3 is filled, the excimer lamp 20 is operated (i.e. is switched ON) while the sample fluid is maintained within the volume 3 of the measuring cell 2 while the excimer lamp 20 is in operation.

When the measurement of conductivity and temperature is to be taken the excimer lamp 20 is switched off for a predetermined first period of time e.g. for 25 ms. After the measurement of conductivity and temperature is done the excimer lamp 20 is switched ON again. This cycle may be repeated, for example, every ten seconds until the control device determines that the stabilization of the oxidation reaction has been reached as described above.

At this phase the total organic carbon content of the sample fluid on the basis of the conductivity and the temperature related to the sample fluid is determined. As soon as the stabilization of the oxidation reaction is determined (as explained above in connection with the description of the control device), the excimer lamp 20 is switched OFF in order to avoid excessive and unnecessary radiation of the interior of the measuring cell 2.

That is, there is no inflow into the volume 3 of the measuring cell 2 and no discharge from the volume 3 measuring cell 2 during the oxidation reaction and the determination of the TOC. Further, the temperature related to the sample fluid used for compensating the conductivity measurement of the sample fluid in the calculation of the TOC is estimated as likewise explained above.

The invention claimed is:

1. A device for measuring a total organic carbon content of a sample fluid, comprising:
   a casing that accommodates:
      a measuring cell defining a volume for receiving the sample fluid;
      an excimer lamp arranged to emit radiation into the volume of the measuring cell, with the emitted radiation having a main wavelength that is suitable to cause an oxidation reaction of organic carbon compounds in the sample fluid contained within the volume of the measuring cell;
      a pair of electrodes arranged to measure a conductivity of the sample fluid in the volume of the measuring cell;
      a first temperature sensor located on the measuring cell;
      at least one second temperature sensor arranged to measure a temperature at a location other than at the measuring cell, wherein the at least one second temperature sensor is arranged to measure a temperature related to the sample fluid, before the oxidation reaction of organic compounds in the sample fluid is started and/or at a location upstream of the volume of the measuring cell;
   wherein said device is configured to introduce the sample fluid whose related temperature is measured by said at least one second temperature to said measuring cell for oxidation by said excimer lamp.

2. The device according to claim 1, further comprising:
   a control device configured to determine, based on the conductivity and a temperature related to the sample fluid, that the oxidation reaction of organic carbon compounds in the sample fluid has stabilized, and configured to switch off the excimer lamp in accordance with a result of determination.

3. The device according to claim 2, wherein the control device is configured to estimate the temperature related to the sample fluid in the volume of the measuring cell using a measuring result of the first temperature sensor and, if provided, of a second temperature sensor.

4. The device according to claim 1, wherein the device comprises at least one valve arranged to block a flow into or out from the volume of the measuring cell.

5. The device according to claim 1, wherein the main wavelength of the radiation emitted by the excimer lamp is between 150 nm and 200 nm.

6. The device according to claim 1, wherein at least a part of an internal surface of the device exposed to the radiation from the excimer lamp comprises a compound that can transform the radiation into a radiation having at least one wavelength that is different from the main wavelength.

7. The device according to claim 6, wherein the at least one wavelength that is different from the main wavelength is in a range between 180 nm and 280 nm.

8. The device according to claim 6, wherein the compound includes at least one element of the Lanthanides group, in association with at least one of Yttrium, Phosphate or Aluminum Borate.

9. The device according to claim 1, further comprising:
   a catalyzing substance provided in an interior space of the casing to accelerate decomposition of ozone within a chamber of the casing.

10. The device according to claim 9, wherein the catalyzing substance comprises Platinum, Palladium, Copper (II) oxide, activated Carbon, Manganese dioxide ($MnO_2$) or a combination thereof.

11. The device according to claim 9, wherein the catalyzing substance is provided as a paint, a coating, pellets, beads, powder, a 2D or 3D mesh, a plate, a sheet, a foam, a porous structure or as a combination thereof.

12. The device according to claim 1, wherein the measuring cell is made from or includes quartz permeable for the radiation in a range of at least between 150 nm and 280 nm.

13. The device according to claim 1, wherein the volume of the measuring cell is less than 1.0 ml.

14. A method of measuring the total organic carbon content of a sample fluid using the device according to claim 1, wherein the method comprises the steps of:

supplying the sample fluid into the volume of the measuring cell, stopping the supply of the sample fluid into the volume, operating the excimer lamp, maintaining the sample fluid in the volume of the measuring cell while the excimer lamp is in operation, determining the total organic carbon content of the sample fluid on a basis of the conductivity and a temperature related to the sample fluid, switching off the excimer lamp in accordance with a result of determination, and discharging the sample fluid from the volume of the measuring cell.

15. The method of measuring the total organic carbon content of the sample fluid according to claim 14, wherein the method further comprises the step of:

estimating a temperature of the sample fluid using a measuring result of the first temperature sensor and, if provided, of a second temperature sensor, and using this estimated temperature as the temperature related to the sample fluid.

16. The device according to claim 1, wherein the main wavelength of the radiation emitted by the excimer lamp is 172 nm, with a half bandwidth of +/−8 nm.

17. The device according to claim 6, wherein the at least one wavelength that is different from the main wavelength is in a range between about 190 nm and about 250 nm.

18. The method of measuring the total organic carbon content of the sample fluid according to claim 14, wherein the excimer lamp is switched off when it is determined that the oxidation reaction of organic carbon compounds in the sample fluid has stabilized.

\* \* \* \* \*